US006459770B1

(12) United States Patent
Tybinkowski et al.

(10) Patent No.: US 6,459,770 B1
(45) Date of Patent: *Oct. 1, 2002

(54) BACKLASH-RESISTANT DRIVE ASSEMBLY FOR COLLIMATOR IN A CT SCANNER

(75) Inventors: Andrew P. Tybinkowski, Boxford; Ronald E. Swain, Reading; Brian M. McDermott, Tewksbury; Jonna A. Gillis, Saugus, all of MA (US)

(73) Assignee: Analogic Corporation, Peabody, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/837,334

(22) Filed: Apr. 18, 2001

Related U.S. Application Data

(63) Continuation-in-part of application No. 09/552,141, filed on Apr. 14, 2000, now Pat. No. 6,301,304.
(60) Provisional application No. 60/233,703, filed on Sep. 19, 2000.

(51) Int. Cl.$^7$ ............................. G21K 1/02; F16H 55/18
(52) U.S. Cl. ..................... 378/147; 378/150; 74/441; 74/409; 411/231
(58) Field of Search ..................... 378/147, 148, 378/149, 150, 151; 74/440, 441, 409; 411/231, 273

(56) References Cited

U.S. PATENT DOCUMENTS

| | | | |
|---|---|---|---|
| 4,962,518 A | 10/1990 | Spongr et al. | 378/148 |
| 5,054,041 A | 10/1991 | Hampel | 378/150 |
| 5,680,795 A | * 10/1997 | Parsons | 74/441 |
| 5,732,596 A | 3/1998 | Erikson et al. | 74/441 |
| 5,839,321 A | 11/1998 | Siemons | 74/441 |
| 6,301,334 B1 | * 10/2001 | Tybinkowski et al. | 378/147 |

* cited by examiner

*Primary Examiner*—Drew A. Dunn
(74) *Attorney, Agent, or Firm*—McDermott, Will & Emery

(57) ABSTRACT

An assembly including a base and first and second spaced-apart shafts secured to the base and extending generally perpendicular to an elongated aperture of the base. A carrier includes a first support member slidingly receiving the first shaft, a second support member receiving the second shaft, and an elongated opening extending between the support members and generally perpendicular to the shafts. The elongated opening of the carrier is for aligning with the aperture of the base and an elongated slit of a collimator supported on the carrier for passage of an x-ray beam therethrough. A backlash-resistant nut assembly is threadingly received on a threaded portion of the second shaft and secured to the second support member.

16 Claims, 4 Drawing Sheets

BACKLASH-RESISTANT DRIVE ASSEMBLY FOR COLLIMATOR IN A CT SCANNER

CROSS-REFERENCE TO RELATED APPLICATIONS

The present application claims priority to co-pending Provisional U.S. patent application Ser. No. 60/233,703, filed Sep. 19, 2000, and is a continuation in part of U.S. patent application Ser. No. 09/552,141, filed Apr. 14, 2000, now U.S. Pat. No. 6,301,304. Both of said prior applications are incorporated herein by reference.

TECHNICAL FIELD

The present invention relates to mechanical drive assemblies, and in particular to those which are used to effect precise movement of a slit plate in scanning and imaging devices.

BACKGROUND OF THE INVENTION

X-ray imaging devices generally employ a collimated beam of radiation which is directed from a focal spot through an object to be scanned, such as a live human or animal patient, or a package to be inspected. A bank of radiation-sensitive detectors is located opposite the focal spot, with the object to be scanned between the focal spot and the detectors. The focal spot and detectors may be fixed relative to one another on a gantry which rotates about the object to be scanned. The detectors receive radiation which has passed through the object and which has therefore been attenuated to varying degrees as. a function of the density of structures within the object and in the radiation path. The detectors generate signals which correspond to the detected density values, and these signals are used to map the object so that the internal structures can be seen.

The radiation beam is collimated by passage of the beam through a slit in a radiation-opaque plate. Typically the plate contains a number of slits of differing widths, so that the beam can be collimated to different widths. For convenience, the slit plate is generally moved into the desired position by translation in a direction transverse to the direction of the beam (generally referred to as the z-direction).

It is important that the slit through which the radiation beam passes to be collimated be located properly relative to the focal spot and the detectors so as to admit precisely as much radiation as can be detected by the detectors, for maximum data acquisition for each scan of the object. If the slit is not properly aligned with the focal spot and the detectors; some of the radiation pass through the object but may not be received by the detectors. Any radiation which passes through the object without being detected subjects the object to radiation exposure without providing useful imaging data, and this is undesirable.

It is also important that movement of the slit plate be smooth, without backlash, accurate and precise. This is especially critical in scanners which may rotate at speeds greater than one revolution per second.

In prior art scanners, the slit plate is typically mounted on a slide which is adapted for travel along a set of parallel shafts. The slide is driven by a drive mechanism, such as a precision leadscrew, which is mounted to a stepper motor. Misalignment of the shafts, of the slide on the shafts, and binding of the leadscrew, commonly occur because it is difficult to maintain these structures in precise alignment. Because each structure is independently mounted, alignment of all three is a costly and time-consuming undertaking and must be checked and repeated frequently.

It would therefore be an advancement in the art of precision drive assemblies to overcome the disadvantages of the prior art.

SUMMARY OF THE INVENTION

According to one aspect of the invention, there is provided a backlash-resistant sliding assembly for supporting a collimator. The assembly includes a base having an elongated aperture for passage of an x-ray beam therethrough, a first shaft secured to the base and extending generally perpendicular to the aperture of the base, a second shaft spaced from, and extending substantially parallel to the first shaft, the second shaft rotatably secured to the base and having a threaded portion and at least one non-threaded portion. The assembly also includes a carrier adapted to support a collimator having at least one elongated slit, the carrier including a first support member having a bore slidingly receiving the first shaft, a second support member having a bore receiving the non-threaded portion of the second shaft, and an elongated opening extending between the support members and generally perpendicular to the shafts. The elongated opening of the carrier is for aligning with the aperture of the base and an elongated slit of a collimator for passage-of an x-ray beam therethrough.

The assembly further includes a ball bearing sleeve positioned between the second support member and the non-threaded portion of the second shaft for allowing the second shaft to rotate with respect to the second member and for allowing the second member to slide on the non-threaded portion of the second shaft. A backlash-resistant nut assembly is threadingly received on the threaded portion of the second shaft and secured to the second support member.

The backlash-resistant nut assembly preferably comprises a first nut portion with a threaded bore, and a second nut portion having a threaded bore concentric with the threaded bore of the first nut portion, means for mutual engagement of the first and second nut portions, and means for biasing the first and second nut portions apart.

According to one aspect, the second shaft includes a second non-threaded portion separated from the first non-threaded portion by the threaded portion, and the carrier further includes a third support member received on the second non-threaded portion of the second shaft. The drive assembly further includes a ball bearing sleeve positioned-between the third support member and the second non-threaded portion of the second shaft for allowing the second shaft to rotate with respect to the third support member and for allowing the third support member to slide on the second non-threaded portion of the second shaft.

According to another aspect, the drive assembly further includes bearing outer sleeves positioned between the second and the third support members of the carrier and the ball bearing sleeves.

These and other objects and advantages of the invention will in part be obvious and will in part appear hereinafter. The invention accordingly comprises the composition and apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be had to the following detailed description taken in connection with the accompanying drawings, in which.

Like elements in the FIGURES are indicated by like reference numerals.

DETAILED DESCRIPTION OF THE DRAWINGS

The drive assembly of the present invention provides several advantages over prior art drive mechanisms. By combining the driving mechanism with the slide or shaft on which a driven member travels, one can eliminate relative movement between the driver and the driven member. This arrangement reduces the number of independently mounted parts which must be independently secured and provides a more smooth movement of the driven member.

Such a drive assembly is particularly useful in precision drive mechanisms, including the drive mechanisms used in imaging equipment in which beam collimation is carried out by movement of a slit plate relative to an x-ray beam. Movement of the slit plate must be accurate, repeatable and precise throughout all operating speeds and temperatures of the imaging equipment.

Figure 1:
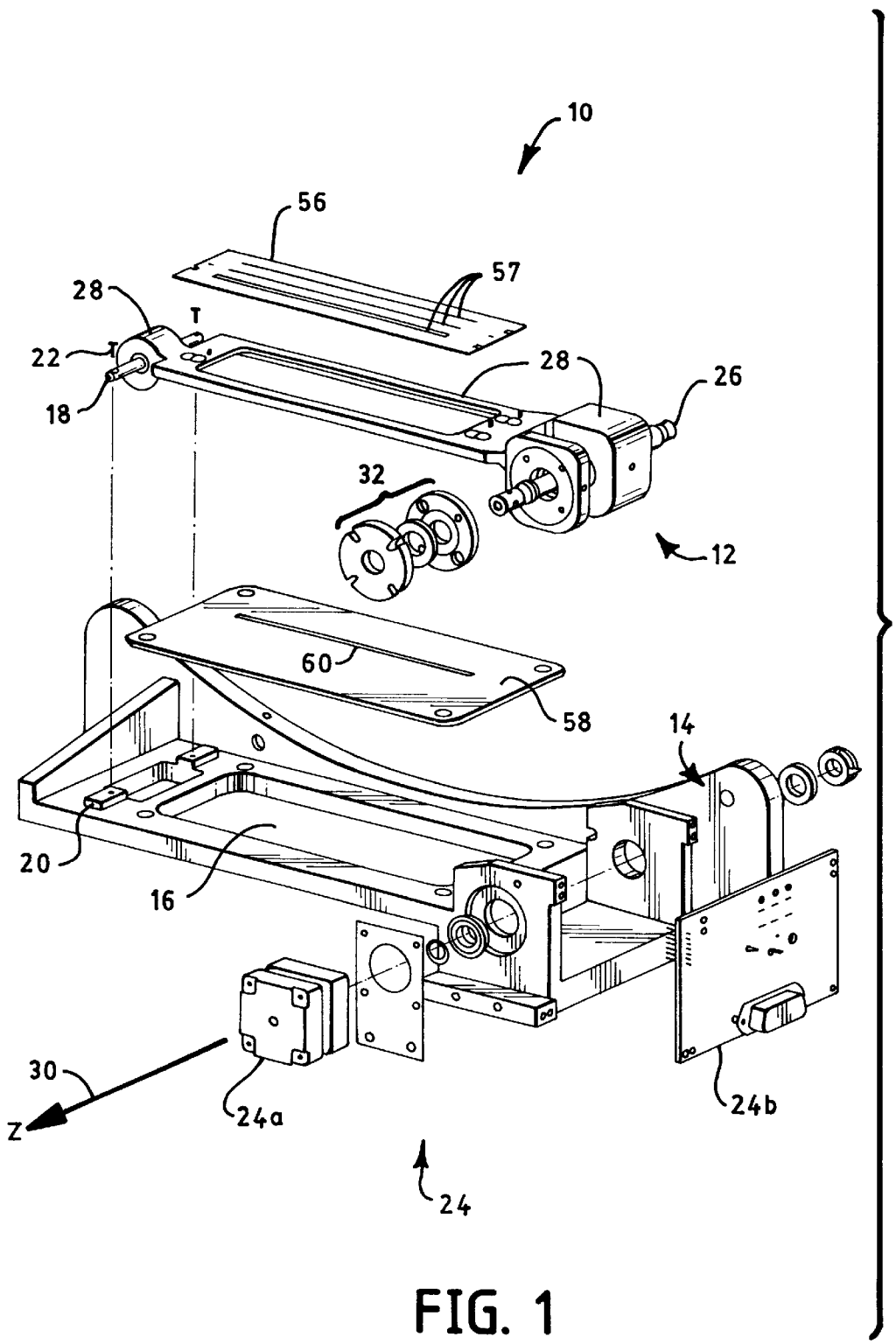
FIG. 1 is an exploded view of a collimator system of an x-ray imaging device which includes a combination slide/drive assembly according to one aspect of the present invention.

FIG. 1 illustrates a collimator assembly 10 of an x-ray imaging apparatus which includes a drive assembly 12 according to the invention. The assembly includes a base 14, which is typically made of cast and machined aluminum or brass. The base includes an aperture 16 for admission of a radiation beam from a focal spot of an x-ray source (not shown).

A first shaft. 18 is secured to blocks or pads 20 at one side of the aperture on the base with screws or like fasteners 22. A driver 24, shown in FIG. 1 as a stepper motor 24a with associated controller circuitry 24b, is also mounted to the base. The driver is rotatably coupled to a second shaft 26 which is substantially parallel to the first shaft 18. A carrier 28 extends between the shafts and is disposed over the aperture 16 in the base. The carrier is adapted to slide along the shafts 18, 26 in the direction of z axis 30 and is preferably made of cast aluminum or brass.

Figure 2:
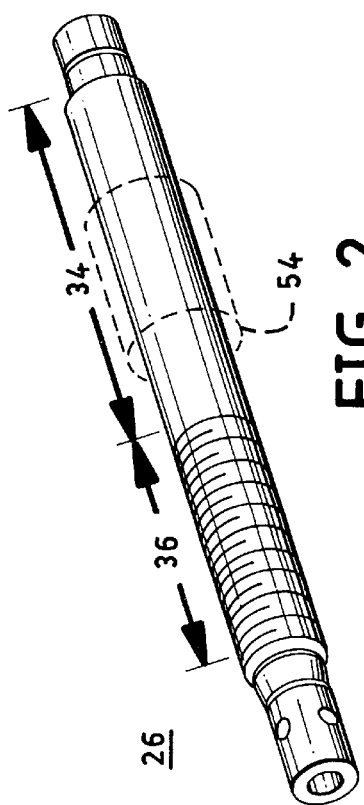
FIG. 2 is a perspective view of the second drive shaft shown in FIG. 1.

According to the invention, the second shaft 26 is coupled to the driver 24 via a backlash-resistant nut assembly 32. As shown in FIG. 2, the second shaft 26 includes a nonthreaded portion 34 and a threaded portion 36. The non-threaded portion 34 of the shaft 26 is adapted for sliding engagement with the carrier, whereas the threaded portion 36 engages with the nut assembly 32, which is fixed to the carrier 28.

Figure 3:
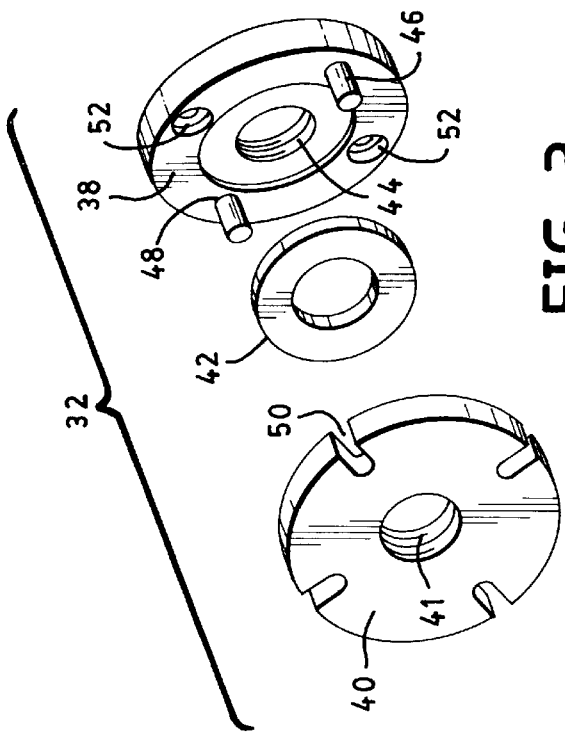
FIG. 3 is an exploded view of the backlash-resistant nut assembly shown in FIG. 1.

The nut assembly 32 is shown in FIG. 3 and includes a first nut portion 38, a second nut portion 40, and a wave washer.42 disposed between them. The first-nut portion 38 has a threaded bore 44 which engages with the threaded portion 36 on the second shaft 26. The second nut portion 40 also has a threaded bore 41 which engages with the threaded portion 36 of the second shaft. The assembly also includes fasteners 46, such as dowel pins, which fit into holes 48 in the first nut portion and slots 50 in the second nut portion. The fasteners join the nut portions together around the wave washer 42, which biases the first and second nut portions away from each other. Means for biasing the nut portions apart other than a wave washer can be used, such as a coiled compression spring. The combined tension and compression of the nut assembly which is created by the counteracting forces of the wave washer 42 and the joined first and second nut portions 38, 40 eliminates substantially all play between the threads of the nut assembly and the threaded portion 36 of the second shaft and prevents any backlash in the movement of the nut over the threaded portion of the shaft 26.

The first nut portion 38 includes counterbored holes 52 for receiving fasteners or screws for joining the nut assembly to the carrier, as shown in FIG. 1. The first and second nut portions of the assembly are preferably made of an easily machinable metal, such as brass or phosphor bronze.

Figure 4:
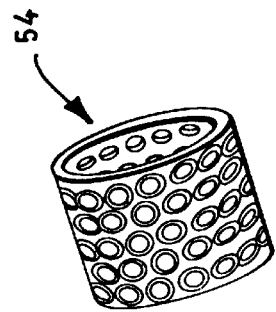
FIG. 4 is a perspective view of a ball bearing sleeve which may be used on the shafts. to reduce friction.

To reduce friction and facilitate smooth movement of the carrier over the shafts, a ball bearing sleeve 54 may be disposed over each of the shafts. A typical ball bearing sleeve is illustrated in FIG. 4 and in phantom on the shaft of FIG. 2. The ball bearing sleeve 54 includes several apertures extending through the wall of the sleeve. A ball bearing is disposed in each aperture and is movable therein without becoming disengaged from the aperture, so that the ball bearing seems to float within the apertures. The ball bearings provide rolling contact between the shaft inside the sleeve and the carrier outside of the sleeve and substantially reduce the friction between these components.

The collimator assembly 10 includes a slit plate 56 which is disposed in the carrier 28 so as to be positioned over the beam aperture in the base. The slit plate 56 includes multiple slits 57 having different widths, for defining beams of different thicknesses in the z direction. The carrier and slit plate move along z axis 30 in response to travel of the nut assembly 32 over the second shaft 26.

A mask plate 58 is fixed to the base beneath the carrier 28 and is disposed over the aperture 16 in the base. The mask plate includes a single slit 60. In operation, the carrier 28 is moved in the z axis direction by operation of the motor 24a so that one of the slits 57 in the slit plate 56 is aligned with the slit 60 in the mask plate, thereby allowing a collimated beam of radiation to pass through the aperture in the base to an object to be scanned and to a detector bank (not shown) beyond the object to be scanned.

The motor 24a preferably comprises a stepping motor controlled by a controller 24b having a counter for calculating which of the plurality of slits 57 of the collimator 56 is aligned with the slit 60 of the mask plate 58 based upon the stepped rotation of the motor. A suitable controller and counter combination is shown, for example, in U.S. Pat. No. 5,550,886 to Dobbs et al. entitled "X-ray Focal Spot Movement Compensation System", which is assigned to the assignee of the present disclosure and which is incorporated herein by reference in its entirety.

Figure 5:
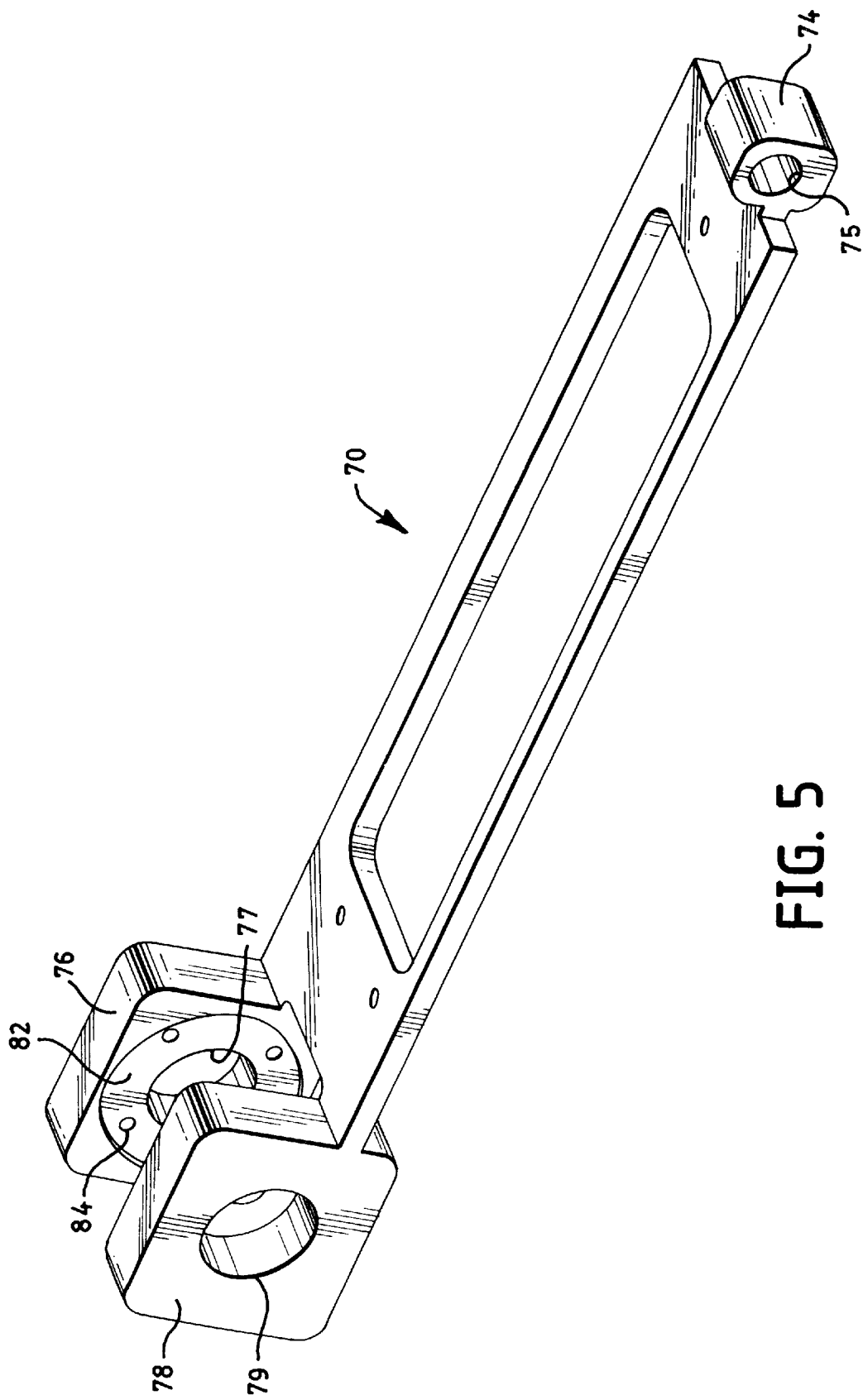
FIG. 5 is a perspective view of an alternative carrier for use with the collimator assembly of FIG. 1.
Figure 6:
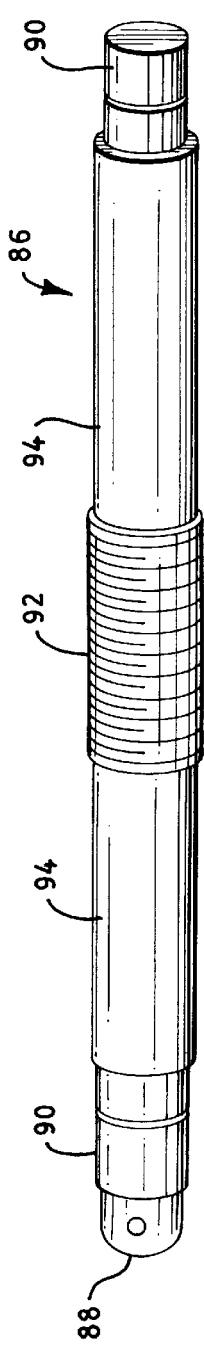
FIG. 6 is a perspective view of an alternative second shaft for use with the carrier of FIG. 5 and the collimator assembly of FIG. 1.

Referring now to FIGS. 5 through 8, an alternative carrier 70 and drive shaft assembly 72 for use with the collimator assembly of FIG. 1 is shown. Referring to FIG. 5, the carrier 70 is preferably made of cast aluminum or brass and includes a first support member 74 having a bore 75 for slidingly receiving the ball bearing sleeve 54 of the first shaft 18. The carrier 70 also includes second and third spaced-apart support members 76, 78 having bores 77, 79, respectively, for slidingly receiving linear-rotary bearings 80 of the drive shaft assembly 72 of FIG. 7.

The second and third support members 76, 78 are each relatively-wide, and provide additional stability for the carrier 70 as the carrier slides on the drive shaft assembly 72. The second support member 76 includes an annular recess 82 and fasteners holes 84 for receipt of the backlash resistant nut assembly 32. As shown, the annular recess 82 faces the third support member 78 such that, when assembled, the nut assembly 32 is positioned between the support members 76, 78 to provide further stability.

Figure 7:
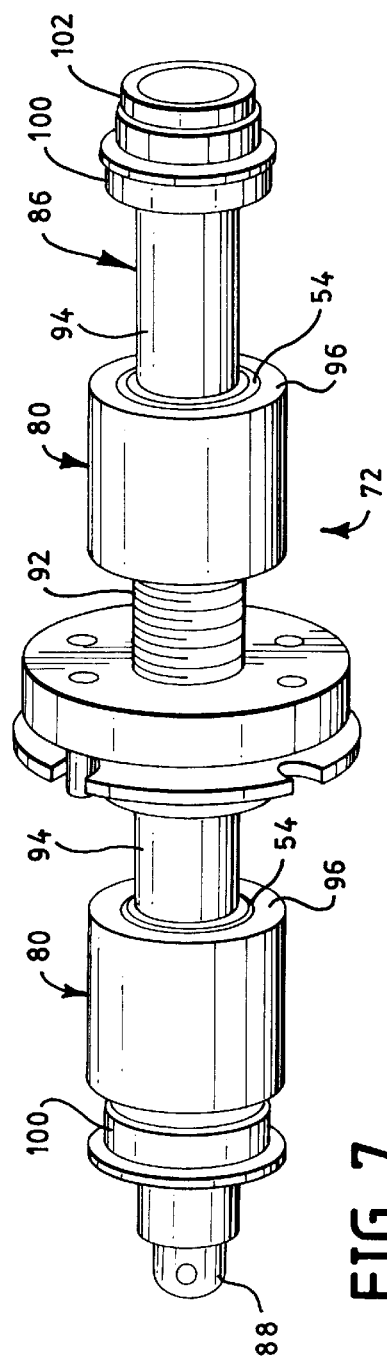
FIG. 7 is a perspective view of a drive shaft assembly including the shaft of FIG. 6, for use with the carrier of FIG. 5 and the collimator assembly of FIG. 1.

Referring to FIG. 7, the drive shaft assembly 72 includes a second shaft 86, which is similar to the second shaft 26 of FIGS. 1 and 2, for supporting the carrier 70 on the base 14 of the collimator assembly 10. The second shaft 86 includes a first end 88 that is formed to be coupled to the driver 24 for turning the shaft. The shaft 86 also includes journals 90 adjacent opposite ends of the shaft, a centrally located threaded portion 92, and non-threaded portions 94 between the threaded portion and the journals.

As shown in FIG. 7, each of the non-threaded-portions 94 of the shaft 86 slidingly and rotatingly receive the linear-rotary bearing 80, which are in turn for being received in the bores of the support members 76, 78 of the carrier 70. The threaded portion 92 of the shaft 86 engages with the backlash resistant nut assembly 32, which is in turn for-being fixed to the annular recess 82 of the third support member 78 of the carrier 70.

Figure 8:
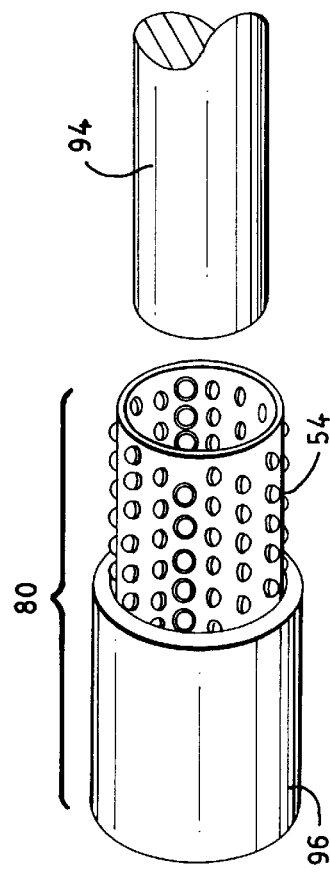
FIG. 8 is an exploded perspective view of a linear-rotary bearing and a portion of the shaft of the drive shaft assembly of FIG. 7.

Each linear-rotary bearing 80 includes an inner ball bearing sleeve 54 received on the shaft 86, and an outer sleeve 96 received on the inner ball bearing sleeve, as also shown in FIG. 8. The linear-rotary bearings 80 allow the shaft 86 to rotate with respect to the support members 76, 78 of the carrier 70 as the motor 24 turns the shaft 86. The linear-rotary bearings 80 also allow the support members 76, 78 of the carrier 70 to linearly slide with respect to the shaft 86 as the backlash resistant nut assembly 32 moves along the threaded portion 92 of the shaft 86. Preferred linear-rotary bearings are available, for example, from Berg Manufacturing of East Rockaway, NY (http://www.wmberg.com).

Referring again to FIG. 7, the drive shaft assembly also includes rotary bearings 100, and a thrust bearing 102 received on the journals 90 of the second shaft 86 for rotatably mounting the drive shaft assembly 72 on the base 14 of the collimator assembly 10.

Because certain changes may be made in the above apparatus without departing from the scope of the invention herein disclosed, it is intended that all matter contained in the above description or shown in the accompanying drawings shall be interpreted in an illustrative and not a limiting sense.

What is claimed is:

1. A backlash-resistant sliding assembly for supporting a collimator, comprising:

a) a base having an elongated aperture for passage of an x-ray beam therethrough, b) a first shaft secured to the base and extending generally perpendicular to the elongated aperture of the base, c) a second shaft spaced from, and extending substantially parallel to the first shaft, the second shaft rotatably secured to the base and having a threaded portion and at least one non-threaded portion;

d) a carrier adapted to support a collimator having at least one elongated slit, the carrier including,
      a first support member having a bore slidingly receiving the first shaft,
      a second support member having a bore receiving the non-threaded portion of the second shaft, and
      an elongated opening extending between the support members and generally perpendicular to the shafts, the elongated opening for aligning with the aperture of the base and an elongated slit of a collimator for passage of an x-ray beam therethrough;

e) a ball bearing sleeve positioned between the second support member and the non-threaded portion of the second shaft for allowing the second shaft to rotate with respect to the second member and for allowing the second member to slide on the non-threaded portion of the second shaft; and f) a backlash-resistant nut assembly threadingly received on the threaded portion of the second shaft and secured to the second support member.

2. An assembly according to claim 1, wherein the backlash-resistant nut assembly comprises:
   first and second nut portion threadingly received on the threaded portion of the second shaft;
   pins extending through the first nut portion and the second nut portion; and
   a compression spring disposed between the first and second nut portions.

3. An assembly according to claim 2, wherein the first nut portion is fixed to the second support member of the carrier.

4. An assembly according to claim 2, wherein the pins extend through holes in the first nut portion and radial slots in the second nut portion.

5. An assembly according to claim 2, wherein the compression spring comprises a wave washer.

6. An assembly according to claim 1, further comprising an outer sleeve positioned between the second support member and the ball bearing sleeve.

7. An assembly according to claim 1, further comprising a mask plate fixed to the base beneath the carrier and over the elongated aperture of the base, wherein the mask plate includes a single elongated slit extending generally parallel with the elongated aperture of the base.

8. An assembly according to claim 1, further comprising a collimator supported on the carrier and having at least one elongated slit for collimating an x-ray beam.

9. An assembly according to claim 8, wherein the collimator includes a plurality of elongated slits of varied widths for collimating an x-ray beam.

10. An assembly according to claim 1, further comprising a rotary motor coupled to the second shaft.

11. An assembly according to claim 10 wherein the motor comprises a stepper motor.

12. A computed tomography scanner including an assembly according to claim 1, and further including:
   an annular gantry rotatable about a rotation axis;
   a beam source mounted within the gantry and having a focal spot for emitting an x-ray beam through the rotation axis; and
   an array of x-ray detectors for receiving the x-ray beam from the focal spot;
   wherein the assembly is mounted within the gantry between the focal spot and the detectors; and a collimator supported on the assembly for collimating the x-ray beam.

13. A backlash-resistant sliding assembly for supporting a collimator, comprising:
- a) a base having an elongated aperture for passage of an x-ray beam therethrough,
- b) a first shaft secured to the base and extending generally perpendicular to the elongated aperture of the base,
- c) a second shaft spaced from, and extending substantially parallel to the first shaft, the second shaft rotatably secured to the base and having a threaded portion and at least one non-threaded portion;
- d) a carrier adapted to support a collimator having at least one elongated slit, the carrier including,
  - a first support member having a bore slidingly receiving the first shaft,
  - a second support member having a bore receiving the non-threaded portion of the second shaft, and
  - an elongated opening extending between the support members and generally perpendicular to the shafts, the elongated opening for aligning with the aperture of the base and an elongated slit of a collimator for passage of an x-ray beam therethrough;
- e) a ball bearing sleeve positioned between the second support member and the non-threaded portion of the second shaft for allowing the second shaft to rotate with respect to the second member and for allowing the second member to slide on the non-threaded portion of the second shaft; and
- f) a backlash-resistant nut assembly threadingly received on the threaded portion of the second shaft and secured to the second support member, wherein:

the carrier further includes a third support member received on the at least one non-threaded portion of the second shaft; and the drive assembly further includes a ball bearing sleeve positioned between the third support member and the non-threaded portion of the second shaft for allowing the second shaft to rotate with respect to the third support member and for allowing the third support member to slide on the non-threaded portion of the second shaft.

14. An assembly according to claim 13, further comprising an outer sleeve positioned between the third support member and the ball bearing sleeve.

15. An assembly according to claim 13, wherein the at least one non-threaded portion of the second shaft comprises two non-threaded portions separated by the threaded portion, wherein each non-threaded portion receives one of the second and third support members of the carrier.

16. A computed tomography scanner including an assembly according to claim 13, and further including:
- an annular gantry rotatable about a rotation axis;
- a beam source mounted within the gantry and having a focal spot for emitting an x-ray beam through the rotation axis; and
- an array of x-ray detectors for receiving the x-ray beam from the focal spot;
- wherein the assembly is mounted within the gantry between the focal spot and the detectors; and
- a collimator supported on the assembly for collimating the x-ray beam.

* * * * *